United States Patent [19]

Szabo et al.

[11] 4,283,413
[45] Aug. 11, 1981

[54] METHOD FOR INHIBITING AGGREGATION OF HUMAN THROMBOCYTES

[75] Inventors: Tibor Szabo; László Institoris; Gábor Kovács; István Stadler; Béla Kószegi, all of Budapest, Hungary

[73] Assignee: Chinoin Gyogyszer es Vegyeszeti Termekek Gyara RT., Budapest, Hungary

[21] Appl. No.: 102,649

[22] Filed: Dec. 12, 1979

Related U.S. Application Data

[63] Continuation of Ser. No. 929,223, Jul. 31, 1978, abandoned.

[30] Foreign Application Priority Data

Aug. 3, 1977 [HU] Hungary ............................ Ci 1762

[51] Int. Cl.³ ............................................ A61K 31/34
[52] U.S. Cl. ................................ 424/285; 260/346.22
[58] Field of Search .................... 260/346.22; 424/285

[56] References Cited

U.S. PATENT DOCUMENTS 3,933,892   1/1976   Chadha et al. .................. 260/346.22

Primary Examiner—Henry R. Jiles
Assistant Examiner—Bernard Dentz
Attorney, Agent, or Firm—Hubbell, Cohen, Stiefel & Gross

[57] ABSTRACT

New compounds and a process for making the same, for use in inhibiting aggregation in human blood and inhibiting the growth of tumors, said compounds being of the general formula:

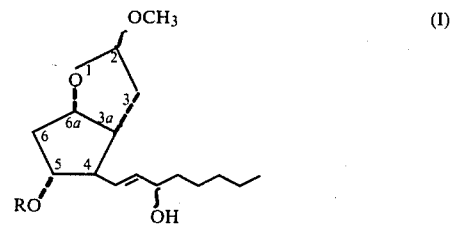

wherein R is hydrogen, alkanoyl, substituted alkanoyl, aralkanoyl or aroyl and ⇌ represents $\alpha$ or $\beta$ steric position or $\alpha$ and $\beta$ position, with the provision that if R stands for p-phenyl-benzoyl then methoxy in the position 2 may stand only in $\alpha$ or only in $\beta$ steric position.

2 Claims, No Drawings

METHOD FOR INHIBITING AGGREGATION OF HUMAN THROMBOCYTES

This is a continuation, of application Ser. No. 929,223, filed July 31, 1978 and now abandoned.

The present invention relates to compounds of the general formula I

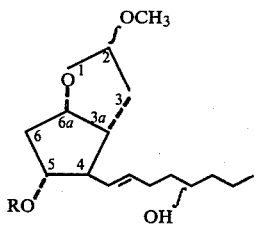

and a process for the preparation thereof.

In the formula I

R is hydrogen, optionally substituted alkanoyl, aralkanoyl or aroyl,

∽ stands for α- or β- steric position or α and β steric position.

The hydroxy group in allyl position of the compounds of the general formula I may be of α- or β configuration ("S" and "R" according to the stereospecification of Cahn-Ingold-Prelog). Similarly methoxy attached to carbon atom 2 of the cyclopentano(b)furan group may be in exo- or endo steric position. If the methoxy group of the cyclopentano(b)furan group on the furan ring considered as quasiplanar is on the same side of the ring as the hydrogens in the positions 3a and 6a, it is in exo steric position; if it is on the other side, the methoxy group is in endo steric position.

According to the invention a process is provided to prepare all epimers falling under the formula I in a pure state having stereochemically homogeneous configuration.

A compound of the general formula I having hydrogen in the place of R is known (JACS 95, 6853/1973/), but when preparing the compound an epimeric mixture was obtained (on carbon atom 2) and nothing is disclosed about the preparation of the individual epimers in pure state.

We have now found, that compounds of the general formula I may be prepared by a much simpler method and better yield compared with the processes known from the prior art, by reacting compounds of the general formula II

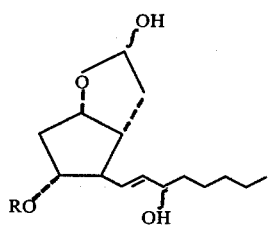

with methanol in the presence of an acid catalyst.

R is in the general formulae I and II hydrogen, optionally substituted alkanoyl, aralkanoyl, or aroyl, the alkanoyl groups contain 1 to 20 carbon atoms and may be straight or branched chained and optionally substituted or unsubstituted. The alkylene chain of the aralkanoyl groups may contain 1 to 20, preferably 1 to 4 carbon atoms, and are optionally substituted or unsubstituted and straight or branched chained. The aromatic group of the aralkanoyl and aroyl groups may consist of one or several hetero- or homocyclic rings or ring systems, wherein the rings may contain as heteroatoms one or several nitrogen, sulfur or oxygen atoms and/or may be substituted or unsubstituted. The aromatic rings may be formed by condensing the rings with each other or by being bound by chemical bonds. Alkanoyl, aralkanoyl and aroyl groups may optionally be substituted by one or several substituents, such as halogens, such as fluorine, chlorine, bromine, or iodine, alkoxy, such as lower alkoxy, such as methoxy, ethoxy, propoxy or butoxy, alkyl, such as lower alkyl, such as methyl, ethyl, propyl, butyl, nitro, amino, differently substituted amino, cyano, alkylsulfone or arylsulfone.

The starting materials of the general formula II are prepared according to a process disclosed in the Hungarian Patent Application No.: CI-1654. Compounds of the general formula II as prepared according to Hungarian Patent Application CI-1654 have α or β stereochemical configuration considering the position of the hydroxy group of allyl position, and the exo:endo isomer ratio is about 70:30 considering 2-hydroxy and these compounds are epimers on carbon atom 2.

As the compounds of the general formula II used as starting materials are semi-acetals, the compounds may be converted to acetals, i.e. compounds of the general formula I by reacting them with methanol in the presence of an acid catalyst.

The reaction may be carried out in the presence of inert solvents, such as chlorinated hydrocarbons: dichloromethane ether type solvents, such as diethylether, tetrahydrofuran, or other aprotic solvents, such as dimethylsulfoxide, or dimethylformamide, but the methanol may preferably be used in excess as a solvent.

The acid catalyst used in the reaction may be an organic or inorganic acid.

Inorganic acids, such as concentrated hydrochloric acid solution, hydrochloride acid gas, Lewis acids, preferably borotrifluoride etherate are preferred in an amount of 0.001–0.1 equivalents.

The reaction of the invention may be carried out within a wide temperature range. One may proceed at a lower temperature than room temperature and also at a higher temperature, but the reaction is most preferably carried out at room temperature. If the reaction is carried out at a temperature much higher than the room temperature, the reaction is preferably carried out in a closed vessel.

If R in the starting materials of the general formula II has a different definition from hydrogen, then the epimeric acetal esters obtained after the acetal formation may be separated by column chromatography. It is particularly preferred, if R in the compounds of the general formula II stands for p-phenyl-benzoyl.

In this case the reaction mixture may be subjected after forming acetal with methanol-to column chromatography, on silicagel or other conventional absorbent and as eluting agent preferably a mixture of isopropylether and ethylacetate is used. In the course of the column chromatography the less polar acetal ester containing an exo methoxy group is first eluted, which may be readily crystallized from isopropylether by adding petrolether. The more polar "endo" epimer may also be isolated in a pure state, but cannot be crystallized like the "exo" epimer.

If R stands for hydrogen in the starting material of the general formula II, i.e. if the compound is a triol, then the epimeric methylethers cannot be separated or cannot easily be separated. By using appropriate physicochemical methods such as gas chromatography, NMR spectroscopy the presence of the epimers can be well detected.

The preparation of stereochemically homogeneous compounds of the general formula I wherein R is hydrogen may be carried out in some of the cases by fractionated crystallization when the better crystallizing exomethylether diol precipitates from the epimer-mixture.

Compounds of the general formula I—wherein R is hydrogen—can also be prepared by separating the epimers of the compounds of the compounds of the general formula I, wherein R is optionally substituted alkanoyl, aralkanoyl or aroyl in respect to the 2-methoxy group, by column chromatography followed by hydrolysis or preferably alkoholysis. The ester acetal derivative is preferably stirred in methanol in the presence of potassium carbonate obtaining thus by alkoholysis the desired compound of the general formula I.

The known representatives of the compounds of the general formula I have so far been considered as useful intermediate products of the prostaglandine synthesis and the biological activity thereof has not been investigated. It has now been suprisingly found that the compounds of the invention of the general formula I such as (−)-2,3,3aβ,6aβ-tetrahydro-2-exo-methoxy-5α-hydroxy-4β-(3β-hydroxy-oct-1-trans-enyl)-cyclopentano(b)furan show a valuable biological activity, for example excellent antiaggregation activity and tumour inhibiting activity. The compounds are capable of inhibiting or suspending the aggregation of human thrombocytes induced by different reactants, such as adenosine diphosphate or arachidonic acid in a concentration of 100 μg./ml.-100 ng./ml. This activity is particularly advantageous due to the selective character of the thrombocyte aggregation inhibiting activity of the compounds and no side effects (vessel wall or smooth muscle contraction effects, hypotensive or hypertensive activity) are observed at the given concentration.

Investigation of the aggregation inhibiting activity:

The tests were carried out on human plasma rich in thrombocythes. 1 ml. of plasma was tested by modified Born aggregometer.

1. The aggregation of the control sample was induced by $1 \times 10^{-5}$ mole of adenosine diphosphate (ADT).
2. 79 μmoles (a compound of the general formula I—wherein R is hydrogen are dissolved in TRIS hydrochloric acid buffer (ph=7.5, 0.05 M) and a 100% inhibition was induced.

The same compound induced a 38% inhibition at a concentration of 39 μmoles/ml.

The investigation of tumour inhibiting activity:

The compounds of the general formula I surprisingly effect the growth of tumour cells. The biological activity was investigated on Novikoff hepatoma or Yoshida ascites sarcoma cells in vitro by inhibiting DNA synthesis of tumour cells measured by building in thymidine-$^3$H. The tumour cells were taken out from the animals on the 6$^{th}$ or third day after the inoculation of the tumour and were incubated for 30 minutes with the solution of the compounds of a concentration of 10 to 100 μg/ml. and for 60 minutes with thymidine-$^3$H precursor. The DNA synthesis was inhibited by all compounds to an extent of 20 to 70% even at a concentration of 10 μg./ml.

The inhibition of tumour growth was investigated on Ehrlich ascites carcinoma in vivo. The tumour was inoculated to mice by administering 5 millions of tumour cells intraperitoneally. The treatment was started 24 hours after the inoculation and was repeated daily for 8 days by injecting doses of 1, 2 and 4 mg./kg. intraperitoneally. Every tested compound resulted a prolongation of life of 150-200%.

EXAMPLE 1

(−)-2,3,3aβ,6aβ-Tetrahydro-2-exo-and -endo-methoxy-5α-(p-phenyl-benzoyloxy)-4β-(3β-hydroxy-oct-1-transenyl)-cyclopentano(b)furan To a 500 ml. flask equipped with a stirrer 22.6 g. (50 mmoles) of (−)-2,3,3aβ, 6aβ-tetrahydro-2-hydroxy-5α(p-phenyl-benzoyloxy)-4β-(3β-hydroxy-oct-1-trans-enyl)-cyclopentano(b)furan are added, 203 ml. (5 moles) of anhydrous methanol are added and the mixture is stirred at room temperature until dissolution is complete. After the dissolution the reaction is started by the addition of 0.5 ml. (5 mmoles) concentrated hydrochloric acid solution. The conversion takes place within 10 minutes. 0.84 g. (10 mmoles) of sodium hydrogen carbonate and a few drops of water are then added to the reaction mixture and it is concentrated in vacuo. The residual thick oil is chromatographed on silicagel column consisting of 1130 g. of silicagel, and eluted with a 9:1 mixture of isopropylether and ethyl acetate. The individual fractions are investigated during column chromatography by thin layer chromatography. As eluting agent a 2:1 mixture of isopropylether and ethyl acetate is used. It is developed in phosphoromolibdenic acid. Exo-epimer is eluted first followed by the elution of the endo-epimer.

The epimers are separately evaporated to dryness.

14.4 g. of exo-epimer (62%) and 7.8 g (33.6%) of endo-epimer are obtained.

14.4 g. of exo-epimer are dissolved in 15 ml. of isopropylether under heating, whereafter 60 ml. of petrolether are added slowly to the solution. The mixture is then crystallized at 0° C. The crystals are filtered off, covered by petrolether-isopropylether mixture and it is dried at room temperature. The obtained white needle crystals amount to 13.2 g. M.p.: 75°–76° C. Thin layer chromatography shows: developed on a "Polygramm Sil. G./UV$_{254}$" thin layer plate in a 2:1 mixture of isopropylether and ethyl acetate: R$_f$=0.56. IR peaks at 3400, 2940, 2860, 1720, 1640, 1610, 1280, 1120, 1100, 1050, 750 cm$^{-1}$.

The endo-epimer is an oil. Thin layer chromatography shows R$_f$=0.45.

EXAMPLE 2

(−)-2,3,3aβ,6aβ-Tetrahydro-2-exo- and-endo-methoxy-5α-(p-phenyl-benzoyloxy)-4β-(3α-hydroxy-oct-1-transenyl)-cyclopentano(b)furan To a 50 ml. flask equipped with a stirrer 2.26 g. (5 mmoles) of (−)-2,3,3aβ,6aβ-tetrahydro-2-hydroxy-5β-(p-phenyl-benzoyloxy)-4β-(3β-hydroxy-oct-1-trans-enyl)-cyclopentano(b)furan are added. 20.3 ml. of anhydrous methanol are added, the mixture is stirred until complete dissolution and 0.05 ml. (0.5 mmoles) of concentrated hydrochloric acid solution is added. The reaction is completed in 10 to 20 minutes at room temperature. The hydrochloric acid is then neutralized with 0.084 g. (1 mmole) of sodium hydrogen carbonate and the solvent is removed in vacuo. The crude product is purified and the exo- and endo-epimers are separated on 680 g. silicagel column by chromatography, and as eluting agent a 9:1 mixture of isopropylether and ethyl acetate is used.

The obtained exo-epimer is an oil. Yield: 1.35 g. (58%). It is developed by thin layer chromatography on a "DC-Fertigplatten Kieselgel" plate in a 9:1 mixture of isopropylether and ethyl acetate.

$R_f=0.53$. Developer: phosphoro molibdenic acid.

The obtained endo-epimer is an oil. Yield: 0.8 g. (34.5%). Thin layer chromatography gives under conditions given at the exo-epimer $R_f=0.425$.

EXAMPLE 3

(−)-2,3,3a$\beta$,6a$\beta$-Tetrahydro-2-exo- and-endo-methoxy-5$\alpha$-hydroxy-4$\beta$-(3$\beta$-hydroxy-oct-1-trans-enyl)-cyclopentano(b)furan To a 250 ml. flask 5.4 g. (20 mmoles) of (−)-2,3,3a$\beta$,6a$\beta$-tetrahydro-2,5$\alpha$-dihydroxy-4$\beta$-(3$\beta$-hydroxy-oct-1-trans-enyl)-cyclopentano(b)furan are added followed by the addition of 81 ml. (2 mmoles) of anhydrous methanol. After dissolution 0.2 ml. (2 mmoles) of concentrated hydrochloric acid solution is added to start the reaction and it is monitored by thin layer chromatography. (Eluting agent ethyl acetate, thin layer plate: "Polygramm Sil.G./UV$_{254}$", developer: phosphoro molibdenic acid. The starting material gives a spot at $R_f=0.25$, and the end product gives a spot at $R_f=0.5$. The product has one spot, as exo- and endo- epimers according to carbon atom 2, do not separate. The reaction mixture is neutralized with 0.34 g. (4 mmoles) of sodium hydrogen carbonate in the presence of a few drops of water, whereafter the excess methanol is distilled off in vacuo. The residual oil is chromatographed on a silicagel column weighing 135 g. and eluting with ethyl acetate as eluting agent. 5.2 g. of thick oil is obtained (92%). The oil is subjected to gas chromatography, which show that the exo- and endo-epimers are present in a ratio of 7:3.

The obtained 5.2 g. of oil is dissolved in 11 ml. of isopropylether and 65 ml. of petrolethene added and it is crystallized at 0° C. White crystalline needles are obtained weighing 2.5 g., melting point: 60°14 61° C. The obtained substance is pure exo-epimer.

EXAMPLE 4

(−)-2,3,3a$\beta$,6a$\beta$-Tetrahydro-2-exo-methoxy-5$\alpha$-hydroxy-4$\beta$-(3$\beta$-hydroxy-oct-1-trans-enyl)-cyclopentano(b)furan To a 100 ml. flask 9.3 g. (20 mmoles) of (−)-2,3,3a$\beta$,6a$\beta$-tetrahydro-2-exo-methoxy-5$\alpha$-(p-phenyl-benzoyloxy)-4$\beta$- (3$\beta$-hydroxy-oct-1-trans-enyl)-cyclopentano(b)furan are added and 64 ml. of anhydrous methyl alcohol and 4.15 g. (30 mmoles) of calcinated potassium carbonate are added. The temperature of the reaction mixture is maintained at 40° C. under vigorous stirring. The reaction is monitored by thin layer chromatography on a "Polygramm Sil.G./UV$_{254}$" plate and as eluting agent a 2:1 mixture of isopropylether and ethyl acetate is used. Developing system: phosphoro molibdenic acid. The starting material shows $R_f=0.56$ and the product gives and $R_f=0.15$, while p-phenyl-benzoic acid methylester appears in the zone of the solvent.

When the reaction is completed the reaction mixture is cooled to 0° C., filtered and the filtrate is evaporated in vacuo and the obtained oil is chromatographed in a 2:1 mixture of isopropylether and ethyl acetate on a silicagel column, containing 93 g. of silicagel. The chromatographed product is immediately crystallized. Yield: 5.5 g. (97%). The product is recrystallized from 28 ml. of isopropylether and petrolether is added to obtain white needle crystals (5.1 g.). Melting point: 60°14 61° C.

EXAMPLE 5

(−)-2,3,3a$\beta$,6a$\beta$-Tetrahydro-2-endo-methoxy-5$\alpha$-hydroxy 4$\beta$(3$\beta$-hydroxy-oct-1-trans-enyl)-cyclopentano(b)furan The process is carried out according to Example 4. As starting material (−)-2,3,3a$\beta$,6a$\beta$-tetrahydro-2-endo-methoxy-5$\alpha$-(p-phenyl-benzoyloxy)-4$\beta$-(3$\beta$-hydroxy-oct-1-trans-enyl) -cyclopentano(b)furan is used. $R_f$ value of the starting material is 0.40 under the circumstances given in Example 4 and $R_f$ of the product is 0.15. After chromatographing 5.3 g. (93%) of colourless thick oil is obtained. The product is homogeneous from stereochemical point of view according to gas-chromatography and NMR analysis.

EXAMPLE 6

(−)-2,3,3a$\beta$,6a$\beta$-Tetrahydro-2-methoxy-5$\alpha$-hydroxy-4$\beta$-(3$\alpha$-hydroxy-oct-1-trans-enyl)-cyclopentano(b)furan The process is carried out according to Example 3, but as starting material an epimer containing hydroxy of allyl position in $\alpha$-configuration is used. $R_f$ on "Poligramm Sil.G./UV$_{254}$"(ethyl acetate) in a system of phosphoro molibdenic acid is 0.18 and the product appears at $R_f$ 0.40. Exo- and endo-epimers according to carbon atom 2 do not separate like in Example 3 but their presence can be detected by gas-chromatography. The colourless thick oil weighs 5.3 g. (94%) after chromatography.

What we claim is:

1. A method for inhibiting an aggregation of human thrombocytes in human plasma comprising administering a therapeutically effective amount of a compound of the general formula I:

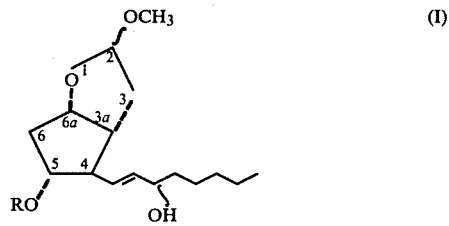

wherein R is hydrogen, alkanoyl, or aralkanoyl and ~ represents $\alpha$ or $\beta$ steric position or a mixture of $\alpha$ and $\beta$ position with the provision that if R stands for p-phenyl-benzoyl then methoxy in the position 2 may stand only in $\alpha$ or only in $\beta$ steric position, in a pharmaceutically acceptable diluent.

2. The method of claim 1, wherein the compound administered is (−)-2,3,3a$\beta$,6a$\beta$-tetrahydro-2-exo-methoxy-5$\alpha$-hydroxy-4$\beta$-(3$\beta$-hydroxy-oct-1-trans-enyl)-cyclopentano(b)furan.

* * * * *

UNITED STATES PATENT AND TRADEMARK OFFICE
CERTIFICATE OF CORRECTION

PATENT NO. : 4,283,413
DATED : August 11, 1981
INVENTOR(S) : Tibor Szabo, et al.

It is certified that error appears in the above—identified patent and that said Letters Patent is hereby corrected as shown below:

Column 1, line 24: "⌣" should read -- ∿ --.

Column 3, line 52: "79 μmoles (a compound" should read -- 79 μmoles of a compound --.

Column 5, line 46: "melting point 60° 14 61° C" should read -- melting point 60-61°C --.

Column 6, line 9: "60° 14 61°C" should read -- 60-61°C --.

Signed and Sealed this

Sixteenth Day of March 1982

[SEAL]

Attest:

GERALD J. MOSSINGHOFF

Attesting Officer     Commissioner of Patents and Trademarks